(12) United States Patent
Murphy et al.

(10) Patent No.: US 8,992,860 B2
(45) Date of Patent: Mar. 31, 2015

(54) SYSTEMS AND METHODS FOR MINIMIZATION OR ELIMINATION OF DIFFUSION EFFECTS IN A MICROFLUIDIC SYSTEM

(71) Applicant: Canon U.S. Life Sciences, Inc., Rockville, MD (US)

(72) Inventors: Brian Murphy, Baltimore, MD (US); Scott Corey, Hydes, MD (US); Alex Flamm, Baltimore, MD (US); Ben Lane, Hydes, MD (US); Conrad Laskowski, Bethesda, MD (US); Chad Schneider, Owings Mills, MD (US)

(73) Assignee: Canon U.S. Life Sciences, Inc., Rockville, MD (US)

(*) Notice: Subject to any disclaimer, the term of this patent is extended or adjusted under 35 U.S.C. 154(b) by 0 days.

(21) Appl. No.: 14/252,234

(22) Filed: Apr. 14, 2014

(65) Prior Publication Data
US 2014/0220584 A1 Aug. 7, 2014

Related U.S. Application Data

(62) Division of application No. 12/758,395, filed on Apr. 12, 2010, now Pat. No. 8,709,356.

(60) Provisional application No. 61/168,395, filed on Apr. 10, 2009.

(51) Int. Cl.
*B01L 3/00* (2006.01)
*C12Q 1/68* (2006.01)
(Continued)

(52) U.S. Cl.
CPC .............. *C12Q 1/6806* (2013.01); *G01N 33/50* (2013.01); *G01N 21/66* (2013.01); *F04B 49/106* (2013.01);
(Continued)

(58) Field of Classification Search
CPC .................. B01L 3/502784; B01L 2300/0816; B01L 2300/0867; B01L 2200/10; B01L 2200/0684; C12Q 2565/629; C12Q 1/6869; C12Q 1/68; C12Q 2563/149; C12Q 2565/301; C12Q 1/6816; C12Q 1/6834; C12Q 1/686; C12Q 1/6825; C12Q 1/6851; C12Q 2563/125; C12Q 2563/155; C12Q 2565/607; C12Q 1/683; B01F 13/0071; B01F 13/0076; B01F 5/0646; B01F 5/0647; B01F 13/0059; B01F 11/0071; B01F 13/0062; B01F 3/0807; B01F 13/0072; B01F 13/0093; B01F 15/0201; B01F 15/024; B01F 5/0655
USPC .............. 422/52, 82.05, 82.06, 82.07, 82.08, 422/82.09, 82.11, 407, 501, 502, 503; 435/164, 165, 283.1, 287.1, 287.2, 435/288.7, 808, 4, 5, 7.2, 7.9; 436/164, 436/165, 172, 174, 518, 805, 809; 204/403.01; 506/3, 39; 359/321; 250/458.1, 559.29, 574; 356/128, 244, 356/246, 300, 326, 414, 416, 445; 430/290, 430/321
See application file for complete search history.

(56) References Cited

U.S. PATENT DOCUMENTS 6,440,725 B1 8/2002 Pourahmadi et al.
6,803,568 B2 10/2004 Bousse et al.
(Continued)

OTHER PUBLICATIONS

Akpa et al., "Study of miscible and immiscible flows in a microchannel using magnetic resonance imaging," Anal. Chem., 79(16)6128-34 (2007) (abstract).

(Continued)

*Primary Examiner* — Dennis M White
(74) *Attorney, Agent, or Firm* — Rothwell, Figg, Ernst & Manbeck, P.C.

(57) ABSTRACT

The present invention relates to systems and methods for minimizing or eliminating diffusion effects. Diffused regions of a segmented flow of multiple, miscible fluid species may be vented off to a waste channel, and non-diffused regions of fluid may be preferentially pulled off the channel that contains the segmented flow. Multiple fluid samples that are not contaminated via diffusion may be collected for analysis and measurement in a single channel. The systems and methods for minimizing or eliminating diffusion effects may be used to minimize or eliminate diffusion effects in a microfluidic system for monitoring the amplification of DNA molecules and the dissociation behavior of the DNA molecules.

16 Claims, 7 Drawing Sheets

(51) Int. Cl.
*B01L 7/00* (2006.01)
*G01N 33/50* (2006.01)
*G01N 21/66* (2006.01)
*F04B 49/10* (2006.01)
*H05B 1/02* (2006.01)
*F04B 49/06* (2006.01)
*G01N 35/00* (2006.01)

(52) U.S. Cl.
CPC ...... *B01L 2300/0861* (2013.01); *B01L 2200/10* (2013.01); *H05B 1/025* (2013.01); *F04B 49/065* (2013.01); B01L 3/502715 (2013.01); B01L 7/525 (2013.01); *B01L 2200/0684* (2013.01); *B01L 2200/141* (2013.01); *B01L 2200/147* (2013.01); *B01L 2300/18* (2013.01); *G01N 2035/00544* (2013.01); B01L 3/502784 (2013.01); *B01L 2300/0816* (2013.01); *B01L 2300/0867* (2013.01); *C12Q 2565/629* (2013.01); *Y10S 435/808* (2013.01); *Y10S 436/805* (2013.01); *Y10S 436/809* (2013.01)
USPC ....... 422/503; 422/52; 422/82.05; 422/82.06; 422/82.07; 422/82.08; 422/82.09; 422/82.11; 422/407; 422/501; 422/502; 436/164; 436/165; 436/172; 436/174; 436/518; 436/805; 436/809; 435/164; 435/165; 435/283.1; 435/287.1; 435/287.2; 435/288.7; 435/808; 435/4; 435/5; 435/7.2; 435/7.9; 205/403.01; 506/3; 506/39; 355/321; 250/458.1; 250/559.29; 250/574; 356/128; 356/244; 356/246; 356/300; 356/326; 356/414; 356/416; 356/445; 430/290; 430/321

(56) References Cited

U.S. PATENT DOCUMENTS

| | | |
|---|---|---|
| 6,848,462 B2 | 2/2005 | Covington et al. |
| 7,214,320 B1 | 5/2007 | Gregori et al. |
| 7,593,560 B2 | 9/2009 | Hasson et al. |
| 2001/0029793 A1 | 10/2001 | Moler et al. |
| 2002/0104759 A1 | 8/2002 | Backhouse |
| 2003/0089605 A1 | 5/2003 | Timperman |
| 2004/0126279 A1 | 7/2004 | Renzi et al. |
| 2005/0161669 A1 | 7/2005 | Jovanovich et al. |
| 2006/0076295 A1 | 4/2006 | Leonard et al. |
| 2006/0150385 A1 | 7/2006 | Gilligan et al. |
| 2006/0272945 A1 | 12/2006 | Manz et al. |
| 2007/0068573 A1 | 3/2007 | Cox et al. |
| 2007/0175756 A1 | 8/2007 | Nguyen et al. |
| 2008/0003588 A1 | 1/2008 | Hasson et al. |
| 2008/0003593 A1 | 1/2008 | Hasson et al. |
| 2008/0003594 A1 | 1/2008 | Hasson et al. |
| 2008/0131327 A1 | 6/2008 | Van Dam et al. |

OTHER PUBLICATIONS

Hasselbrink et al., "High-pressure microfluidic control in lab-on-a-chip devices using mobile polymer monoliths," Anal. Chem., 74(19):4913-8 (2002) (abstract).

Hofmann et al., "Modular approach to fabrication of three-dimensional microchannel systems in PDMS—application to sheath flow microchips," Lab on a Chip, vol. 1, pp. 108-114 (2001).

Lammerink et al., "Modular Concept for Fluid Handling Systems," IEEE, pp. 389-394 (1996).

Sassa et al., "Microprocessing of liquid plugs for bio/chemical analyses," Anal. Chem., 80(16)6206-13 (2008) (abstract).

Schabmueller et al., "Design and fabrication of a microfluidic circuitboard," J. Micromech. Microeng., vol. 9, pp. 176-179 (1999).

Situma et al., "Merging microfluidics with microarray-based bioassays," Biomol. Eng.,23(5)213-31 (2006) (abstract).

Sun et al., "Modular microfluidics for gradient generation," Lab Chip, 8:1536-1543 (2008) (abstract).

Yuen, "SmartBuild—a truly plug-n-play modular microfluidic system," Lab Chip, 8(8):1374-8 (2008) (abstract).

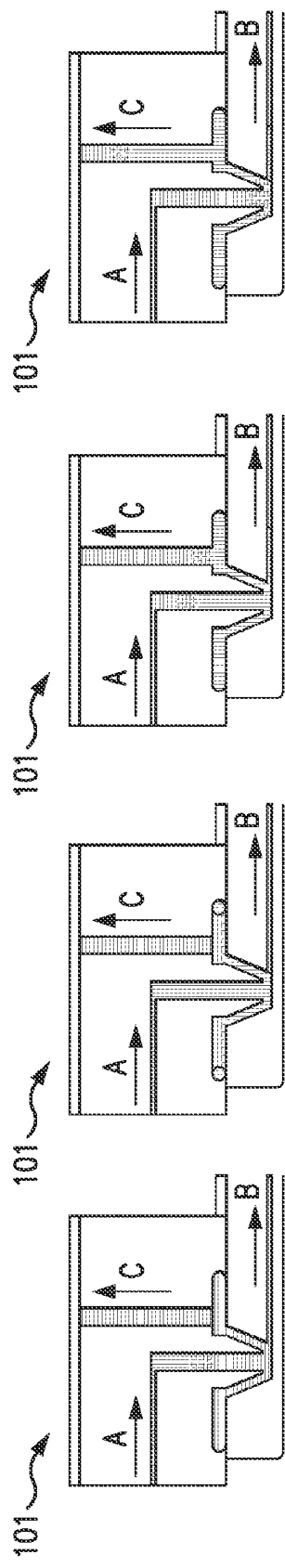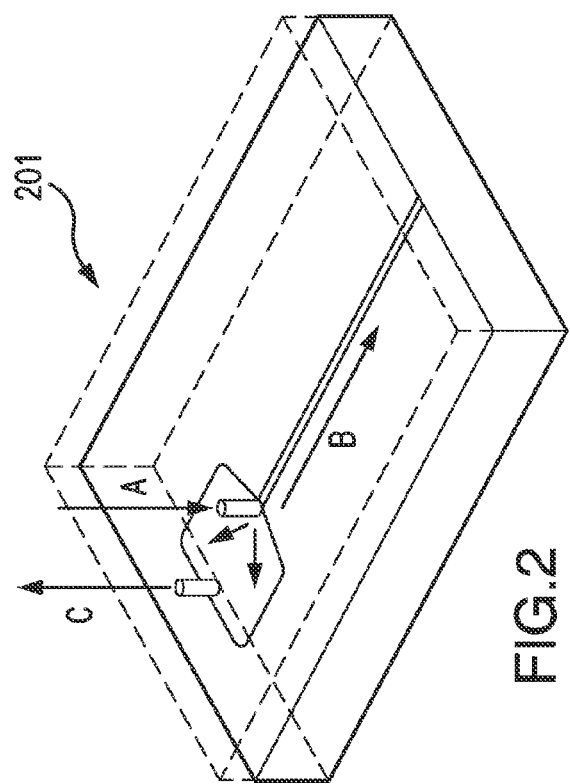

# US 8,992,860 B2

SYSTEMS AND METHODS FOR MINIMIZATION OR ELIMINATION OF DIFFUSION EFFECTS IN A MICROFLUIDIC SYSTEM

CROSS-REFERENCE TO RELATED APPLICATIONS

This application is a divisional of and claims priority to U.S. patent application Ser. No. 12/758,395, filed on Apr. 12, 2010, which claims the benefit of U.S. Provisional Patent Application Ser. No. 61/168,395, filed on Apr. 10, 2009, which is incorporated herein by reference in its entirety.

BACKGROUND

1. Field of the Invention

The present invention relates to systems and methods for minimizing and/or eliminating diffusion effects in a microfluidic system. More specifically, embodiments of the present invention relate to systems and methods for minimizing and/or eliminating diffusion effects in a microfluidic system having one or more channels so that concentration dependent measurements can be made on a segmented flow of multiple miscible fluids in the one or more channels.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase Chain Reaction ("PCR") is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies of the amplified DNA to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA). The process of causing DNA to transition from dsDNA to ssDNA with increasing temperature is sometimes referred to as a "high-resolution temperature (thermal) melt (HRTm)" process, or simply a "high-resolution melt" process. Alternatively, the transition from ssDNA to dsDNA may be observed through various electrochemical methods, which generate a dynamic current as the potential across the system is changed.

Microfluidic chips are being developed for "lab-on-a-chip" devices to perform in-vitro diagnostic testing. The largest growth area is in molecular biology where DNA amplification is performed in the sealed channels of the chip. Optical detection devices are commonly used to measure the increasing amplicon product over time (Real Time PCR) and/or to perform a thermal melt to identify the presence of a specific genotype (High Resolution Thermal Melt). Exemplary disclosures related to the imaging of a microfluidic chip to measure the fluorescent product can be found in commonly-owned U.S. application Ser. No. 11/505,358 to Hasson et al. entitled "Real-Time PCR in Micro Channels" (U.S. Pat. Pub. 2008-0003588) and U.S. application Ser. No. 11/606,204 to Hasson et al. entitled "Systems and Methods for Monitoring the Amplification and Dissociation Behavior of DNA Molecules" (U.S. Pat. Pub. 2008-0003594), the respective disclosures of which are hereby incorporated by reference.

When a fluid is introduced into a channel to measure increasing amplicon product in the fluid over time and/or to identify the presence of a specific genotype in the fluid, it is desirable to minimize and/or prevent contamination of the fluid so that accurate results may be obtained. At the same time, it may be desirable to introduce a series of fluid species into a channel so that a single channel may be used to measure and/or identify multiple fluid species in succession. Minimization and/or prevention of contamination becomes especially difficult when the multiple fluid species are miscible (i.e., capable of being mixed) and are supplied to a single channel in a segmented fashion (i.e., with each species occupying the entire width of the channel and existing axially down or upstream from another of the species, which also occupies the entire width of the channel).

Flow through a microfluidic channel is generally characterized by laminar flow with parabolic velocity profiles. These parabolic velocity profiles indicate that fluid along the walls of the microfluidic channel will move much slower than the fluid at the center of the channel. In flows of only one species of fluid where the same chemical concentration exists at all points in the flow, this variation in fluid velocity as a function of distance from the channel wall has little impact. In flows in which two miscible species of fluid exist in a segmented fashion, the effects of the laminar velocity profile are problematic. In particular, as the fluid in the center of the channel moves faster than the edges, each segment of flow will stretch into the segment immediately downstream of it. This stretching dramatically increases the surface area between each segment of fluid. Due to the different species of fluids being miscible in each other, the increase in surface area increases the rate of diffusion and therefore the potential cross contamination between segments. As a result, downstream measurements that require significant sections of non-diffused fluids may become difficult or impossible to perform due to contamination.

Accordingly, a need exists in the art for systems and methods to ensure that samples can be obtained in microfluidic systems that are free or substantially free from contamination by diffused fluids.

SUMMARY

The present invention relates to systems and methods for minimizing and/or eliminating diffusion effects in a microfluidic system. The present invention allows for concentration dependent measurements to be made on a segmented flow of multiple miscible fluids in a single channel.

In one aspect, the present invention provides a method of collecting, from a continuous flow of two or more miscible fluids sequentially present in a channel, one or more samples that are substantially free from contamination by the other miscible fluids present in the channel. In one embodiment, the method comprises: (a) identifying and monitoring the position of a diffusion region between uncontaminated portions of a first miscible fluid and a second miscible fluid in a first channel; (b) diverting the diffusion region into a second channel; and (c) collecting a portion of the second miscible fluid which is substantially free from contamination by any miscible fluids adjacent to the second miscible fluid. In some embodiments, the monitoring the position of the diffusion region may include monitoring a leading edge and a trailing edge of the diffusion region.

In still other embodiments, the portion of the second miscible fluid substantially free from contamination may be collected in a third channel. The position of the diffusion region may be monitored in relation to an opening of the third channel. In one embodiment, the diverting may begin at or before a leading edge of the diffusion region reaches an opening of the third channel and end after a trailing edge of the diffusion region passes the opening of the third channel. In other embodiments, the second channel may lead to a waste area. In other embodiments, the diverting step may include pulling fluid of the diffusion region from the edge of the first channel, and the collecting step may include pulling fluid of the portion of the second miscible fluid from the center of the first channel.

In some embodiments, the method may further comprise: (d) identifying and monitoring the position of a diffusion region between uncontaminated portions of the second miscible fluid and a third miscible fluid in a first channel; (e) diverting the diffusion region into the second channel; and (f) collecting a portion of the third miscible fluid which is substantially free from contamination by any miscible fluids adjacent to the third miscible fluid. In other embodiments, the method may further comprise monitoring the amplification of DNA in the collected portion of the second miscible fluid, and monitoring the dissociation behavior of the amplified DNA in the collected portion of the second miscible fluid.

In other aspects, the present invention provides a microfluidic system comprising: a first channel, a second channel, a monitoring device, and a fluid flow control system. In one embodiment, the monitoring device identifies and tracks one or more diffusion regions between adjacent miscible fluids of two or more miscible fluids present in the microfluidic system. The fluid flow control system controls the flow of fluid through each of the first and second channels. As two or more miscible fluids are moved through the first channel, the fluid flow control system causes the one or more diffusion regions to flow into an opening of the second channel and causes one or more miscible fluid samples that are substantially free from contamination by adjacent miscible fluids present in the first channel to be collected. In some embodiments, the monitoring device may track a leading edge and a trailing edge of the one or more diffusion regions. In other embodiments, the collected one or more miscible fluid samples may be caused by the fluid flow control system to be collected after a trailing edge of one of the one or more diffusion regions has passed an entrance to a third channel, and the fluid flow control system may cause collection to be stopped before the leading edge of a subsequent diffusion region reaches the entrance to the third channel.

In some embodiments, the fluid flow control system may control the flow of fluid through each of the first and second channels based on the identification and tracking of the one or more regions of diffusion performed by the monitoring device. In other embodiments, the second channel may lead to a waste area. The microfluidic system may comprise a third channel in which the one or more miscible fluid samples are collected. The monitoring device may track a position of the diffusion region in relation to an opening of the third channel.

In another aspect, the present invention provides a genomic analysis system comprising: a microfluidic chip, a monitoring device, and a fluid flow control system. In one embodiment, the microfluidic chip has one or more microfluidic channels and a diffusion effect minimization or elimination system for each of the one or more microfluidic channels. Each of the one or more microfluidic channels passes through a diffusion effect minimization or elimination zone, a PCR processing zone, and a HRTm analysis zone. The diffusion effect minimization or elimination system comprises a first pathway, second pathway and a third pathway. A segmented flow of multiple, miscible fluid species enters through the first pathway. One or more miscible fluid samples that are substantially free from contamination by adjacent miscible fluids present in the first pathway are collected and passed to the PCR processing zone and the HRTm analysis zone through the second pathway. One or more diffusion regions between adjacent fluid species of the segmented flow are diverted to a waste zone through the third pathway. In some embodiments, the monitoring device identifies and tracks the one or more diffusion regions present in the diffusion effect minimization or elimination zone of the microfluidic chip. In other embodiments, the system further comprises a fluid flow control system configured to control the flow of fluid through the diffusion effect minimization or elimination system for each of the one or more microfluidic channels.

In another aspect, a method of collecting a sample from a continuous flow of two or more miscible fluids sequentially present in a channel is provided which comprises identifying the leading region of diffusion between two sequential fluids, monitoring the passage of the region of diffusion through the channel such that once the leading region of diffusion has passed an opening for a second channel a portion of the fluid is collected into a second channel, wherein the collecting of fluid is stopped before the next sequential region of diffusion reaches the opening of the second channel. In an embodiment, the collected sample is free from contamination by the other miscible fluid(s) present in the channel.

In another aspect, a microfluidic system is provided which comprises a first channel, a second channel which is in fluid communication with the first channel, and means for moving a liquid through each of the first and second channels. In one embodiment, the microfluidic system further comprises means for identifying and tracking region(s) of diffusion between two or more miscible fluids present in the first channel, wherein as one or more miscible fluids are moved through the first channel, after the region of diffusion has passed the opening of the second channel, the means for moving a liquid through the second channel is activated to cause a portion of the fluid to enter the second channel, whereby the means for moving a liquid through the second channel is deactivated prior to the next region of diffusion passing the opening of the second channel.

In another aspect, the present invention provides a method of collecting, from a continuous flow of two or more miscible fluids sequentially present in a first microfluidic channel, one or more samples that are substantially free from contamination by the other miscible fluids present in the first channel.

The method comprises flowing the continuous flow of two or more miscible fluids through the first channel for a predetermined time. The predetermined time is sufficient to allow the diffused region of the at least two miscible fluids to pass a collection region of the first channel. The collection region may be a junction of the first channel with a second channel. The method also comprises collecting a portion of one of the miscible fluids, which is substantially free from contamination by any miscible fluids adjacent to the collected miscible fluid, into the second channel. The method further comprises stopping the collection of one of the miscible fluids before a subsequent diffused region reaches the collection region of the first channel. In an embodiment, the predetermined time is determined by using a predetermined flow rate and/or a fixed volume displacement. In another embodiment, the steps of flowing, collecting and stopping are repeated for each sample of miscible fluid which is substantially free from contamination by the other miscible fluids to be collected. In some embodiments, the first channel and the second channel are microfluidic channels.

In another aspect, the present invention provides a system of collecting, from a continuous flow of two or more miscible fluids sequentially present in a first channel, one or more samples that are substantially free from contamination by the other miscible fluids present in the channel. The system comprises the first channel, a second channel, a collection region of the first channel formed at a junction between the first channel and the second channel, and a fluid flow control system that controls the flow of fluid through each of the first and second channels. The fluid flow control system is configured to flow the continuous flow of the two or more miscible fluids through the first channel for a predetermined time. The predetermined time is sufficient to allow the diffused region of the at least two miscible fluids to pass the collection region of the first channel. The fluid flow control system is configured to collect a portion of one of the miscible fluids, which is substantially free from contamination by any miscible fluids adjacent to the collected miscible fluid, into the second channel. The fluid flow control system is further configured to stop the collection of one of the miscible fluids before a subsequent diffused region reaches the collection region of the channel. In some embodiments, the first channel and the second channel are microfluidic channels. In some embodiments, the fluid flow control system is configured to determine the predetermined time by using a predetermined flow rate and/or a fixed volume displacement. In some embodiments, the fluid flow control system is configured to repeat the flowing, collecting and stopping for each sample of miscible fluid which is substantially free from contamination by the other miscible fluids to be collected.

BRIEF DESCRIPTION OF THE FIGURES

The accompanying drawings, which are incorporated herein and form part of the specification, illustrate various embodiments of the present invention. In the drawings, like reference numbers indicate identical or functionally similar elements.

FIGS. 1A-1D provide schematic diagrams of a diffusion minimization system according to one embodiment and show the movement of a segmented flow of multiple fluid species through the system.

FIG. 2 provides a schematic diagram of a diffusion minimization system according to one embodiment.

DETAILED DESCRIPTION OF PREFERRED EMBODIMENTS

Figure 3:
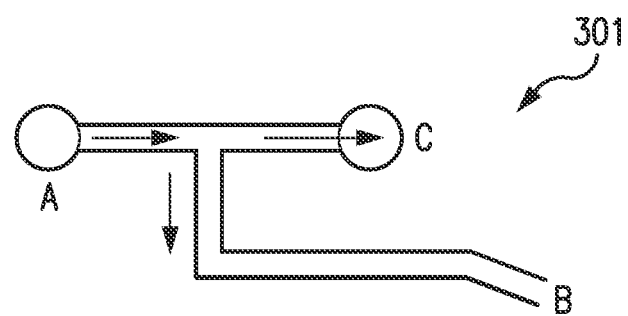
FIG. 3 provides a schematic diagram of a diffusion minimization system according to one embodiment.

Embodiments of the systems and methods of creating and moving segmented flows of multiple miscible fluid species through a microfluidic system, while minimizing diffusion effects between the fluid species, are described herein with reference to figures. In the illustrated embodiments, regions of fluid that become diffused during their transport through the microfluidic system are diverted or vented away from a collection or measurement area such that only regions of fluid with no or little diffusion are sent to the collection or measurement area.

FIGS. 1A-1D illustrate a diffusion minimization system 101 for the elimination and/or minimization of diffusion effects according to one embodiment of the present invention. As shown in FIGS. 1A-D, diffusion minimization system 101 has pathways or channels A-C, which are in fluid communication with each other (i.e., fluid may flow from one of channels A-C into another of channels A-C). In one embodiment, fluid enters the system via pathway A, and leaves the system via pathways B and C. Pathway B may lead to a microfluidic channel where detection, measurement and/or collection may be carried out, and where pure or substantially pure fluid is desirable. Pathway C may lead to a waste area of a microfluidic system. In one embodiment, the fluid entering the system via pathway A may be from one or more test solution reservoirs.

As illustrated in FIG. 1A, in accordance with one embodiment, all pathways of the system 101 are primed with a first species of fluid (shown with horizontal hatch marks). Then a second species of fluid (shown in vertical hatch marks) is introduced to the system via pathway A. A diffusion zone (shown with cross hatches) comprises a portion of the fluid flow that is a mixture of the first and second species of fluid and will exist between a pure portion of the first fluid and a pure portion of the second fluid. As explained above, the extent to which the diffusion occurs may be exacerbated by the parabolic velocity profile of microfluidic flow. In one embodiment, as the diffusion zone nears the entrance to pathway B, the flow into pathway B is shut off to prevent mixed, non-pure fluid from flowing into pathway B and into, for example, the microfluidic channel. The entire diffusion zone is then pumped out through pathway C, as illustrated in FIG. 1B. Once the diffusion zone has passed the entrance to pathway B, pathway B is opened again and the pure second species of fluid is allowed to flow into pathway B, as illustrated in FIG. 1C.

This cycle of accepting regions of pure fluid and venting or diverting regions of diffused fluids may be a repeatable process. For example, FIG. 1C shows another diffusion zone of between a pure portion of second fluid and a pure portion of the next liquid (shown in horizontal hatch marks). As the diffusion zone approaches pathway B, as shown in FIG. 1D, the flow into pathway B is again shut off. As described above, the entire diffusion zone is then pumped out through pathway C, and, once the diffusion zone has passed the entrance to pathway B, pathway B is opened again and the pure fluid is allowed to flow into pathway B. This allows miscible fluids to be transported through a system in segmented form because the contaminated, non-pure diffusion zones between the fluid segments are vented away or discarded before the pure fluids enter a microfluidic channel for detection, measurement and/ or collection. Thus, the diffusion minimization system 101 may also be thought of as a zero dead volume connection between two parts. By placing the connection between the parts where pathway C branches off from pathway B, any dead volume may be eliminated through the repeated flushing of contaminated fluid.

Figure 7:
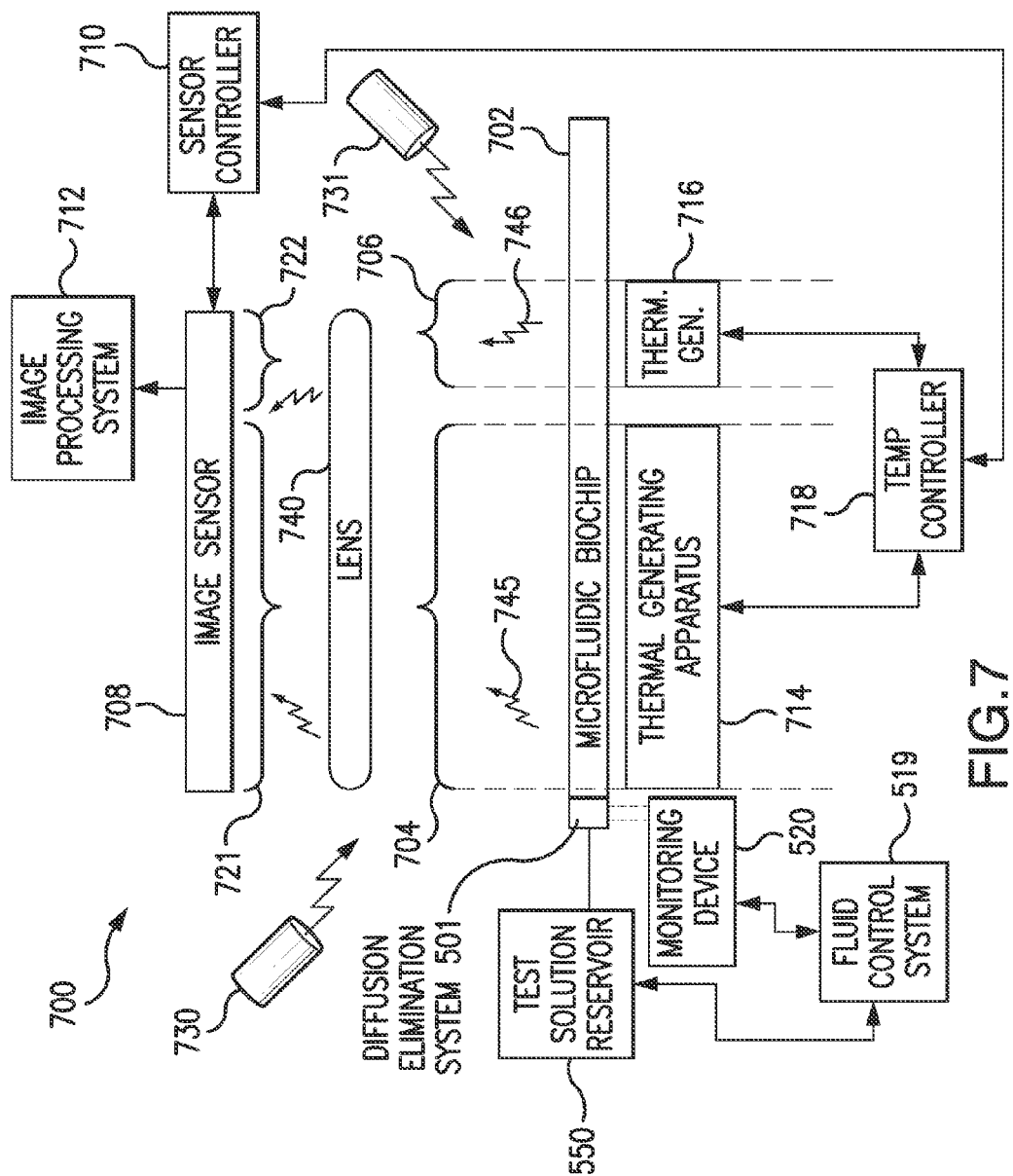
FIG. 7 illustrates a functional block diagram of a microfluidic system according to one embodiment.

One or more diffusion minimization systems 101 may be located in a diffusion minimization or elimination zone of a microfluidic system having one or more microfluidic channels. An example of such a microfluidic system is illustrated in FIG. 7, described in detail below. In one embodiment, one diffusion elimination system 101 is provided for, and is in fluid communication with, each microfluidic channel of a microfluidic system.

Figure 4:
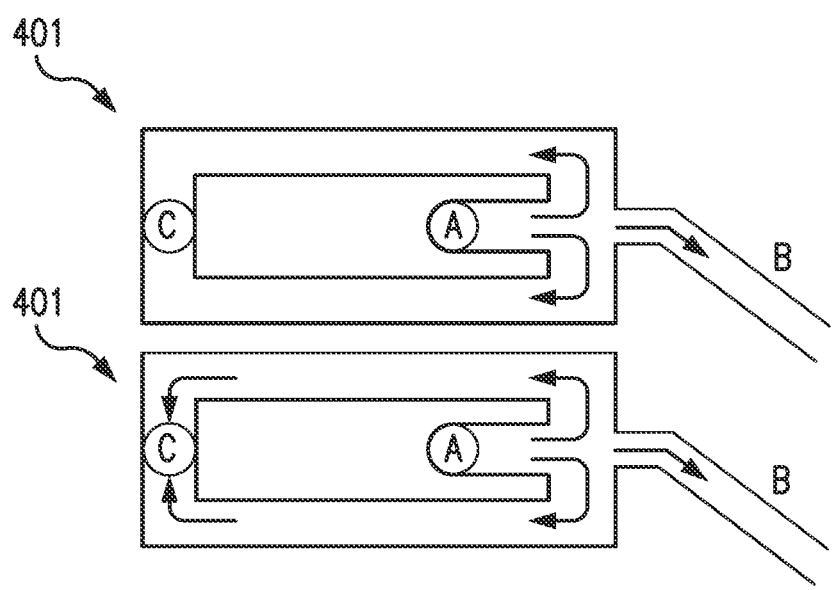
FIG. 4 provides a schematic diagram of a diffusion minimization system according to one embodiment.

Many other embodiments of the diffusion minimization system can also be created. For example, FIGS. 2-4 show diffusion minimization systems 201, 301 and 401, respectively, in accordance with alternative embodiments of the present invention. Similar to the embodiment shown in FIG. 1, in the embodiments shown in FIGS. 2-4, fluid enters the diffusion minimization system via pathway A, portions of fluids of a pure species are pulled into pathway B, and any regions of fluid where diffusion has occurred are vented out of the system through pathway C. As discussed above, the pure species pulled into pathway B may lead to a microfluidic channel in a microfluidic system where detection, measurement and/or collection may be carried out. In addition, an embodiment of the present invention may include alternate configurations of a diffusion minimization system having the same or similar characteristics and results of systems 101, 201, 301 and 401.

Diffusion minimization system 401, as shown in FIG. 4, has the added benefit that fluid is pulled into pathway B, which may lead to a microfluidic channel, from the center of the flow that comes from pathway A. This feature is in contrast to other embodiments which may preferentially pull fluid from the edge of the pathway. Due to the lower velocities associated with the edge of the flow, the fluid at the edges of the flow will be the most diffused and will take the longest to flush clear. Accordingly, pulling fluid from the center of the pathway A into pathway B, as illustrated in FIG. 4, advantageously avoids the diffused boundary layer at the edges of the flow.

The diffusion minimization system embodiments described above share the same premise of preferentially pulling non-diffused regions of fluid off a channel that contains segmented regions of different fluid species, and then venting the diffused regions of flow off to a waste channel. This allows the collection of fluid that is not contaminated via diffusion. The diffusion minimization system embodiments also allow for measurements, which are functions of fluid concentration, to occur from fluid in a single channel which contains multiple miscible flows stacked axially in the channel. As other embodiments of the diffusion minimization system of the present invention may be imagined by making variations on the above geometries, the present invention is not limited to any of the particular embodiments of the diffusion minimization systems described above. Indeed, an embodiment of the present invention may include alternate configurations of a diffusion minimization system having the same or similar characteristics and results of systems 101, 201, 301 and 401.

Figure 5:
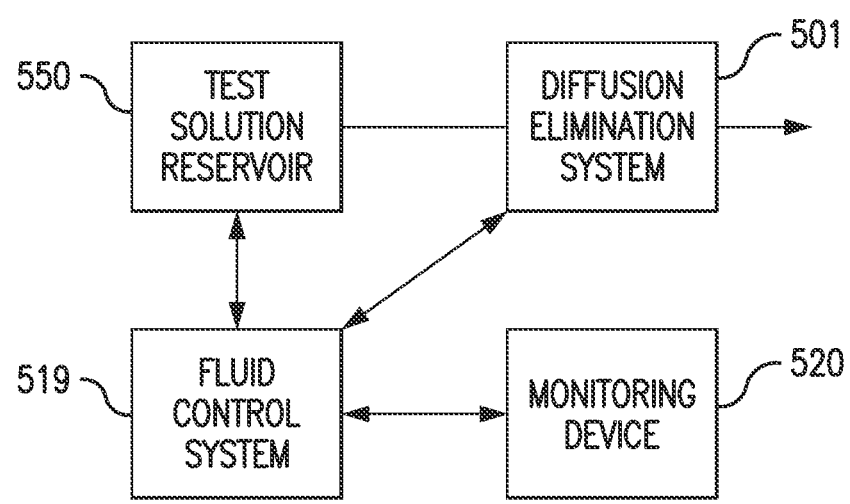
FIG. 5 provides a schematic diagram of system components that may be used in conjunction with a diffusion effect minimization system according to one embodiment.

FIG. 5 shows an example of system components that may be utilized in conjunction with a diffusion minimization system. The diffusion minimization system 501 shown in FIG. 5 represents a diffusion minimization system, such as any of the embodiments described above. For example, diffusion minimization system 501 may be any of systems 101, 201, 301 and 401 of FIGS. 1-4, respectively, or may comprise alternate configurations having the same or similar characteristics and results of systems 101, 201, 301 and 401. Like the diffusion minimization system embodiments described above, system 501 may have channels A-C or some other arrangement of fluid flow channels that allows for selective passage of only pure fluid species segments into, for example, a microfluidic channel while diverting away from the microfluidic channel mixed, non-pure fluids of a diffusion zone between adjacent segments of different fluid species.

As illustrated in FIG. 5, fluid entering the system 501 via pathway A may be from test solution reservoir 550. Fluid flow in each of the channels A-C may be controlled by fluid control system 519. Fluid control system 519 may be configured to provide individual fluid control mechanisms for each of channels A-C. For instance, the individual fluid control mechanisms of fluid control system 519 may be present at the ends of both channels B and C of system 501. Fluid control system 519 may employ any mechanism of fluid control known in the art, such as vacuum pressure, positive pressure, and electrokinetics, to move the fluid species through the diffusion minimization system 501. In some embodiments, fluid control may also be provided by a fluid control mechanism (e.g. vacuum pressure, positive pressure, and electrokinetics) acting on the microfluidic channel through which a pure fluid sample from channel B, for example, would be introduced.

In addition, as illustrated in FIG. 5, one or more monitoring devices 520 may be used to identify and track the movement of the diffusion regions. In some embodiments, fluid control system 519 may use information from the monitoring device 520 to control the flow of the fluids through the channels in the diffusion minimization system. In other embodiments, the monitoring device may comprise a video system to identify and track the movement of the diffusion regions. Although fluid control system 519 and monitoring device 520 are shown in FIG. 5 as being separate from diffusion minimization system 501, fluid control system 519 and monitoring device 520 may be considered part of diffusion minimization system 501. In other embodiments, direct monitoring of the diffusion region is not required if the fluid velocity is known. For example, a set pressure or flowrate may be used to pull the segmented flow of miscible fluids through the channels for a predetermined amount of time which is known to be sufficient to ensure that the diffused regions would be past the collection point. This would allow that the next fluid that is collected into pathway B, for example, is substantially free of contamination from diffusion from other miscible fluids. Similarly, the collection of the non-diffused fluid into pathway B can be stopped prior to the next diffusion region reaching pathway B if the fluid velocity is known. In other embodiments, a fixed volumetric displacement could be used in place of or in addition to flowing the fluid at a given flow rate for a set amount of time. In one example, fluid control system 519 may be configured to use the fluid velocity and/or volumetric displacement to control the flowing, collecting and stopping of the fluids through the channels in the diffusion minimization system 501.

Figure 6:
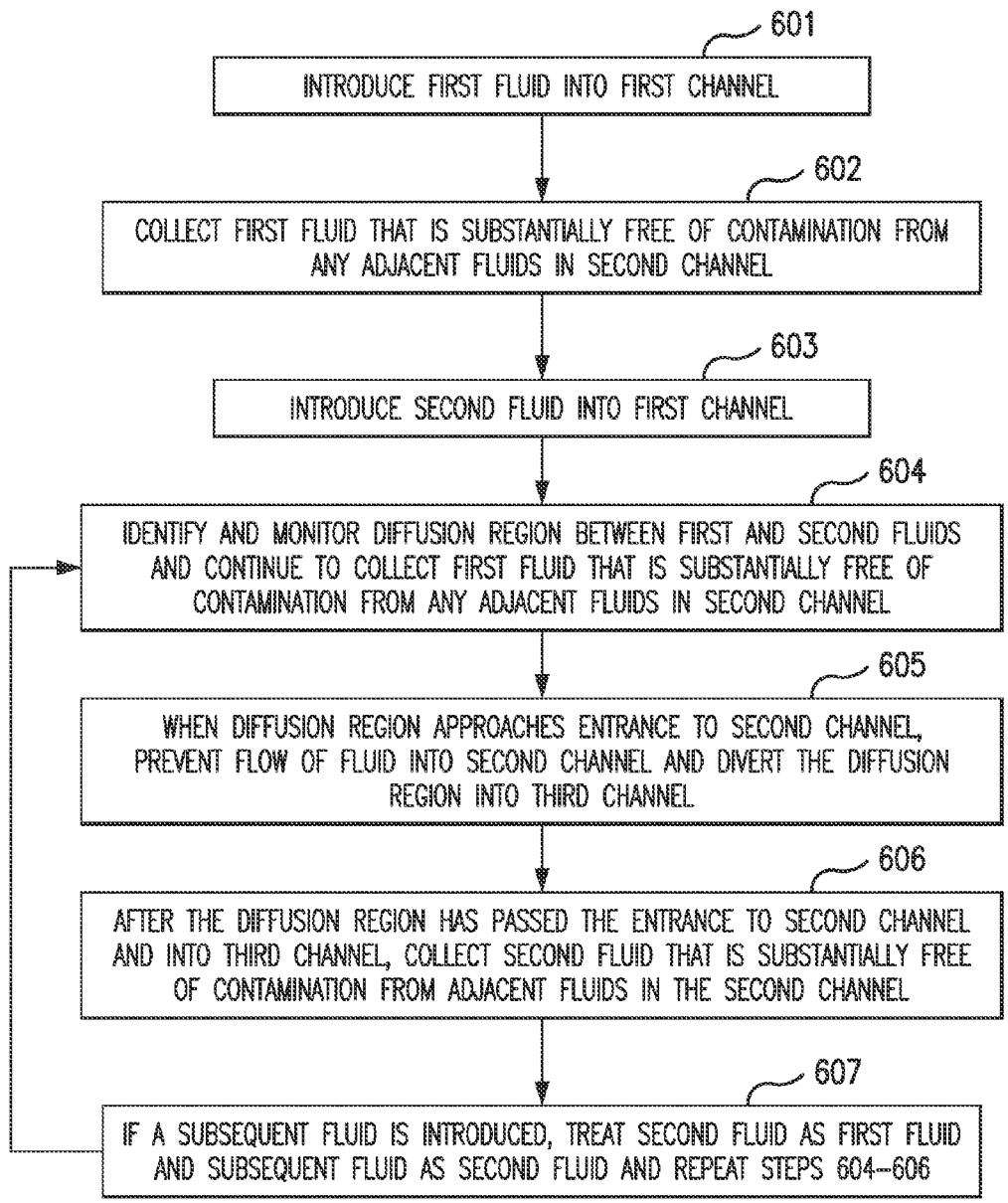
FIG. 6 is a flowchart illustrating a diffusion minimization process according to one embodiment.

Referring now to FIG. 6, a flow chart is provided that illustrates a process of minimizing or eliminating diffusion effects in the segmented flow of multiple, miscible fluid species in accordance with one embodiment of the invention. The process shown in FIG. 6 may be carried out, for example, with any of the diffusion minimization systems 101, 201, 301 or 401 shown in FIGS. 1-4, respectively, or may be carried out with alternate configurations having the same or similar characteristics and results of systems 101, 201, 301 and 401.

In step 601, a first fluid species of a segmented flow of multiple, miscible fluid species is introduced into a first channel (e.g., pathway A of FIGS. 1-4) of a diffusion minimization system. The fluid species of the segmented flow of multiple, miscible fluid species may be provided to the first channel from, for example, test solution reservoir 550. In step 602, the first miscible fluid species (which may be free of contamination) is collected in a second channel (e.g., pathway B of FIGS. 1-4) of the diffusion minimization system. In one embodiment, the second channel may lead to a microfluidic channel for PCR processing and HRTm analysis. In step 603, a second fluid species of the segmented flow of multiple, miscible fluid species is introduced into the first channel. In step 604, the diffusion region between the first and second miscible fluid species is identified, in some exemplary embodiments, via monitoring or via knowledge of other parameters, including a combination of the fluid velocity and the elapsed time, for example. In embodiments where the diffusion region is monitored, the monitoring of the diffusion region may be performed by monitoring device 520. Provided that the diffusion region is not near the entrance to the second channel, the first miscible fluid species may continue to be collected in the second channel.

In step 605, when a diffusion region identified in step 604 is determined to be approaching the entrance to the second channel, for example, via monitoring or via knowledge of other parameters (e.g., fluid velocity and/or volumetric displacement), flow of fluid into the second channel is prevented. For example, a diffusion region may be determined to be approaching the entrance to the second channel by using monitoring device 520, or by using the fluid velocity in combination with the elapsed time, to determine that the leading edge of the diffusion region is within a predetermined distance from the entrance to the second channel. The flow of fluid containing a diffusion region is then diverted into a third channel (e.g., pathway C of FIGS. 1-4), which may be connected to a waste channel or reservoir, instead of being permitted to flow into the second channel.

In step 606, after the diffusion region has been determined to have passed far enough into the third channel and away from the entrance to the second channel, flow of fluid into the second channel is enabled, and the non-diffused portion of the second fluid species is collected in the second channel. For example, a diffusion region may be determined to have passed far enough into the third channel when the monitoring device 520 determines that the trailing edge of the diffusion region is more than a predetermined distance from the entrance to the second channel, or when it is determined that a specific amount of time has elapsed. The second fluid species may be collected in the second channel under control of fluid control system 519. In this way, the third channel acts as a vent through which the contaminated diffusion regions may be removed from the segmented flow of multiple, miscible fluid species so that only uncontaminated portions fluid species are provided for measurement and detection.

In step 607, when a third fluid species of the segmented flow of multiple, miscible fluid species is introduced into the first channel, the steps 604-607 are repeated to vent contaminated, diffusion regions between the adjacent second and third fluid species in the segmented flow and to allow only non-diffused portions of the third fluid species into the second channel.

The process described in connection with the embodiment shown in FIG. 6 begins with introducing a first miscible fluid into the first channel and collecting that first fluid (which would be substantially free of contamination because it is not diffusing into another fluid) into the second channel which may lead to a microfluidic channel in a microfluidic system where detection, measurement and/or collection may be carried out. However, in other embodiments, a flush fluid may be first introduced into all channels followed by the introduction of a second miscible fluid. In this embodiment, the diffusion regions between the first flush fluid and the second fluid may be vented into the third channel and the second fluid, substantially free of contamination, would be collected in the second channel. In still other embodiments, the process could involve identifying and monitoring the position of any diffusion region between uncontaminated portions of adjacent miscible fluids, diverting the diffusion region into the second channel, and collecting the portion of the uncontaminated fluid, in either one or both of the adjacent miscible fluids, for further detection, measurement and/or collection. And, in other embodiments, the diffusion region is not directly monitored, and the fluid velocity and/or fixed volumetric displacement is used determine whether to divert or collect the fluid. For example, a set pressure or flowrate may be used to pull the segmented flow of miscible fluids through the channels for a predetermined amount of time and/or for a predetermined displacement volume which is known to be sufficient to ensure that the diffused regions would be past the collection point. This would allow the next fluid that is collected into the second channel to be substantially free of contamination from diffusion from other miscible fluids. Similarly, the collection of the non-diffused fluid into the second channel can be stopped prior to the next diffusion region reaching the second channel if the fluid velocity and/or displacement volume is known.

FIG. 7 illustrates an example of a microfluidic system 700, according to one embodiment of the invention, in which any of the diffusion minimization systems described above may be incorporated. As shown in FIG. 7, microfluidic system 700 may include a diffusion minimization system 501, a microfluidic chip 702 having a PCR processing zone 704 (i.e., a zone in which DNA is amplified) and a HRTm analysis zone 706 (i.e., a zone in which the dissociation behavior of the amplified DNA is examined).

Figure 8:
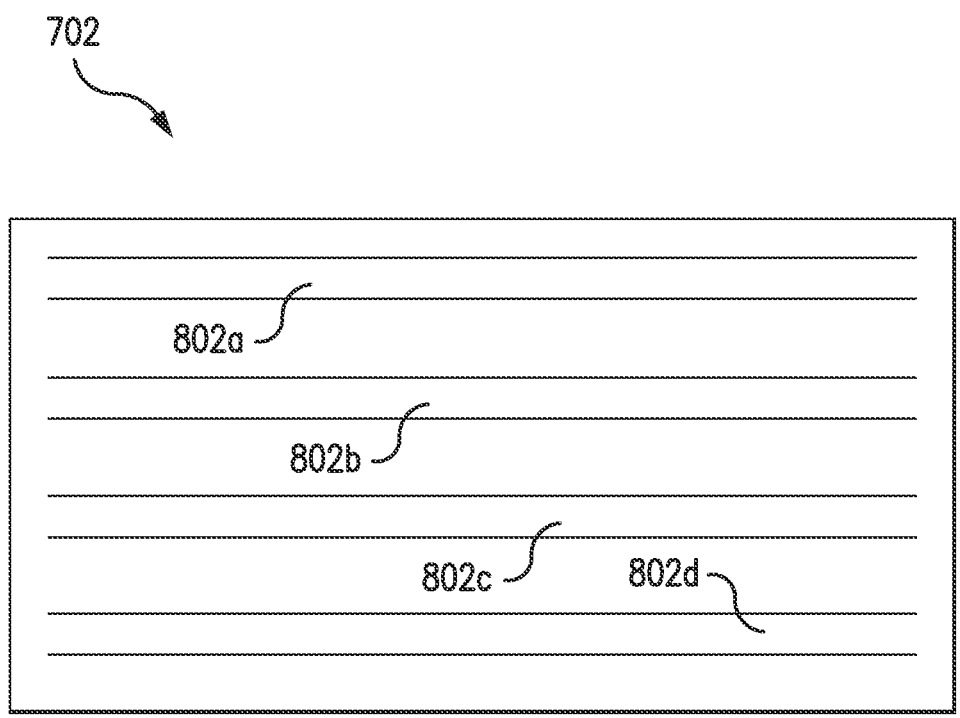
FIG. 8 illustrates a top view of a portion of a microfluidic chip according to one embodiment.

FIG. 8 is a top view of microfluidic chip 702. As shown in FIG. 8, microfluidic chip 702 may include a number of microfluidic channels 802*a-d*. In the example shown, there are 4 microfluidic channels, but it is contemplated that chip 702 may have more or less than 4 channels. As shown, a first portion of each microfluidic channel may be within the PCR processing zone 704 and a second portion of each microfluidic channel may be within the HRTm analysis zone 706.

When microfluidic system 700 is in use, at least one channel 802 receives a sample (or "bolus") of a solution (or "fluid") containing real-time PCR reagents from, for example, diffusion minimization system 501. A force may be used to cause the bolus to travel through the channel such that the bolus traverses PCR zone 704 prior to entering HRTm zone 706. One system and method for performing PCR in a microfluidic device is disclosed in U.S. patent application Ser. No. 11/606,006, filed on Nov. 30, 2006 (U.S. Patent Application Publication No. 2008-0003593), incorporated herein by reference in its entirety.

The microfluidic system 700 may further include an image sensor 708, a controller 710 for controlling image sensor 708, and an image processing system 712 for processing the image data produced by image sensor 708. Image sensor 708 may have a first image sensor region 721 and a second image sensor region 722. Image sensor 708 may be positioned with respect to microfluidic chip 702 such that at least a portion of PCR processing zone 704 is within the field of view of sensor region 721 and at least a portion of HRTm zone 706 is within the field of view of sensor region 722.

Image sensor 708 may be used to (i) produce data corresponding to the intensity of emissions from PCR zone 704, and (ii) produce data corresponding to the intensity of emissions from HRTm zone 706. Thus, microfluidic system 700 may simultaneously monitor (1) the amplification of a sample of DNA, and (2) the dissociation behavior of a different DNA sample.

As illustrated in FIG. 7, microfluidic system 700 may include one or more thermal generating apparatuses. In the embodiment shown, microfluidic system 700 includes a first thermal generating apparatus 714 and a second thermal generating apparatus 716 and a controller 718 for controlling apparatuses 714, 716. Each thermal generating apparatus 714, 716 may be configured to provide heat to and/or absorb heat from chip 702, and, thus, may include one or more heat sources and/or heat sinks. In some embodiments, the first thermal generating apparatus 714 is configured such that while a bolus is within zone 704, thermal generating apparatus 714 cycles the temperature in zone 704 to achieve PCR, and thermal generating apparatus 716 is configured such that, when a bolus enters zone 706, thermal generating apparatus 716 provides a substantially steadily increasing amount of heat to zone 706 to cause the bolus to undergo HRTm analysis (i.e., to cause the dsDNA in the bolus to transition to ssDNA).

In some embodiments, microfluidic system 700 may further include an excitation source 730 (e.g., a laser or other excitation source) for illuminating zones 704 and/or 706. Additional excitation sources (e.g., source 731) may also be employed. Microfluidic system 700 may further include a lens 740 that is disposed between chip 702 and image sensor 708. In such embodiments, lens 740 may be configured to focus onto the first image sensor region 721 light 745 coming from the PCR processing zone 704, and to focus onto the second image sensor region 722 light 746 coming from the HRTm analysis zone 706.

In one embodiment, the diffusion minimization system 501, fluid control system 519 and monitoring device 520 may operate to supply pure or substantially pure fluids to one or more microfluidic channels 802 substantially as described above in connection with FIGS. 1-6. Although microfluidic system 700 is shown with a monitoring device 520, it is not necessary that microfluidic system 700 include a monitoring device. As described herein, a known fluid velocity and/or volumetric displacement may be used instead of direct monitoring of diffusion regions. In FIG. 7, diffusion effect minimization or elimination system 501 is shown as being a component of microfluidic chip 702. However, in other embodiments, diffusion minimization system 501 may be separate from, but fluidically connected to, microfluidic chip 702.

FIGS. 9A-9D show movement of segmented flows of multiple miscible fluid species through an exemplary diffusion effect minimization or elimination system in accordance with an embodiment of the present invention. FIGS. 9A-D show a first channel 901, a second channel 902 and a collection region 903. In the illustrated embodiment, collection region 903 is located at a junction formed between the first channel 901 and the second channel 902. Similar to the embodiments shown in FIGS. 1-4, in the embodiment shown in FIG. 9, fluid enters the diffusion minimization system via first channel 901, portions of fluids of a pure species are pulled into second channel 902, and any regions of fluid where diffusion has occurred are vented out of the system through the portion of first channel 901 past the collection region 903. As discussed above, the pure species pulled into the second channel 902 may lead to a microfluidic channel, such as a PCR channel, in a microfluidic system where detection, measurement and/or collection may be carried out.

In FIGS. 9A-D, the white regions and the dark regions represent different miscible fluids flowing through first and second channels 901 and 902. As illustrated in first channel 901, a diffusion region (represented in gray) exists between adjacent miscible fluids represented by the white and dark segments.

Figure 9A:
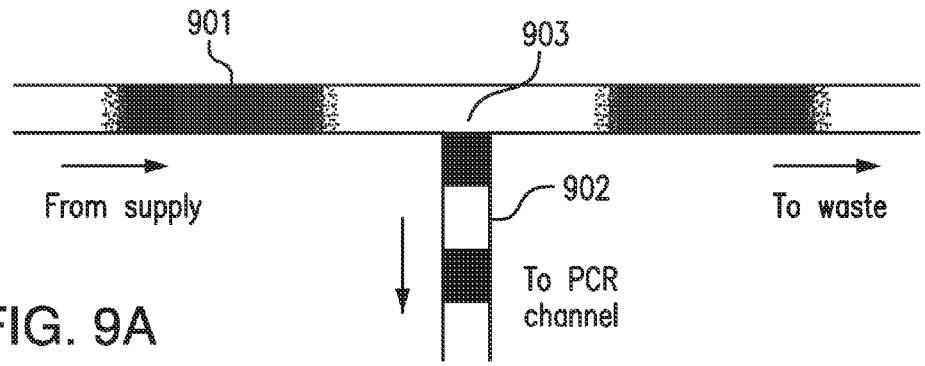
FIGS. 9A-9D show the movement of a segmented flow of multiple fluid species through a diffusion minimization system according to one embodiment.

As illustrated in FIG. 9A, the white and dark fluid segments flow from a supply to the first channel 901. As shown in FIG. 9A, the white fluid segment has been prevented from entering and being collected in the second channel 902 leading, for example, to a PCR channel. The diffusion region between the white fluid segment and the preceding dark fluid segment has passed the collection region 903 and as moved towards a waste area. As shown, the diffusion region between the white fluid segment and the subsequent dark fluid segment is a distance away from the collection region 903.

Figure 9B:
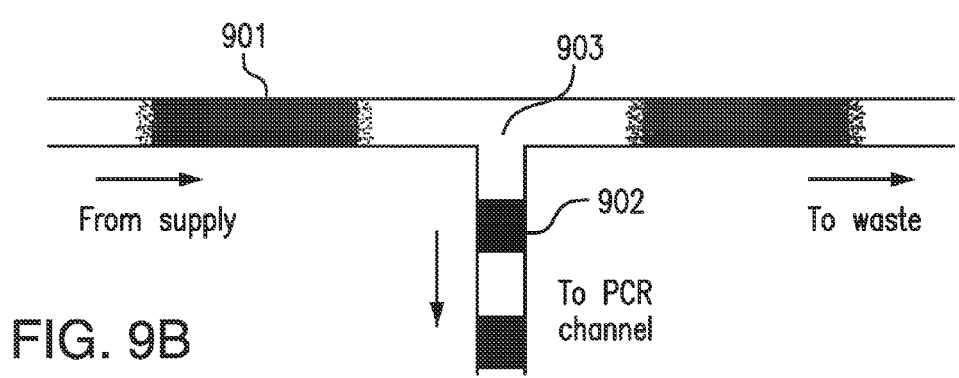
Figure 9C:
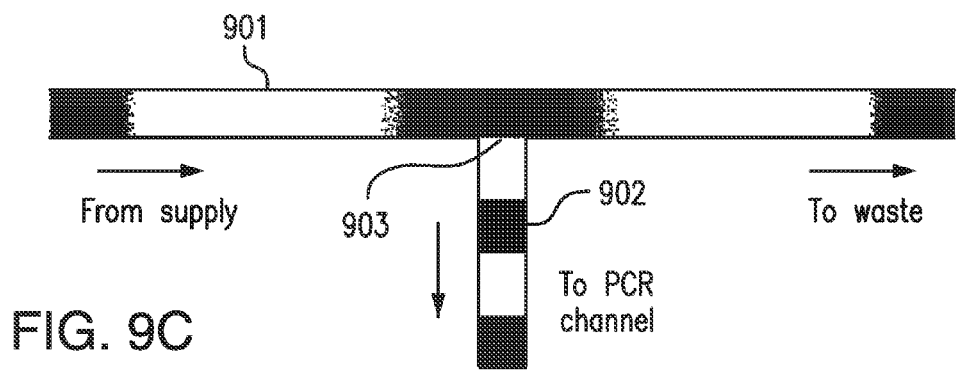

In FIG. 9B, the white fluid segment at the collection region 903 is collected in the second channel 902 leading, for example, to the PCR channel. The white fluid segment collected in the second channel 902 is substantially free from contamination because the diffusion regions between the adjacent dark fluid segments are away from the collection zone. As the diffusion region between the white fluid segment and the subsequent dark fluid segment approaches the collection region 903, fluid is again prevented from entering and being collected in the second channel 902. Accordingly, as shown in FIG. 9C, the diffusion regions passes the collection region 903 without being collected, and flows along the first channel 901 towards the waste area. In this way, the collected fluid samples in the second channel 902 remain substantially free from of contamination of the diffusion region.

Figure 9D:
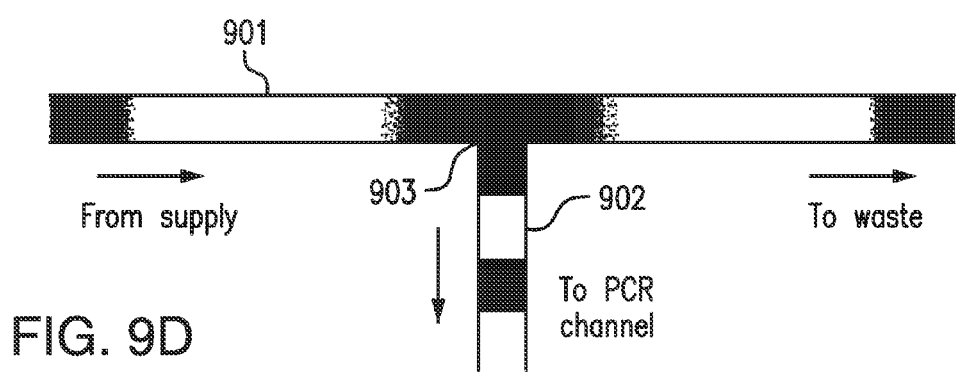

As shown in FIG. 9D, when the diffusion regions between the dark and white fluid segments are away from the collection region 903, the dark fluid segment, which is substantially free from contamination, is collected in the second channel 902, which leads, for example, to the PCR channel. FIGS. 9A-D illustrate that alternating segments of miscible fluids that are substantially free from contamination may be collected and flow into the second channel 902, as illustrated by the sharp white and dark boundaries between segments in that channel.

The embodiment illustrated in FIGS. 9A-D further includes a fluid control system for controlling fluid movement in the channels and the collection of the pure or substantially pure portion of the fluid samples. In some embodiments, the fluid flow control system is configured to flow a continuous flow of the two or more miscible fluids through the first channel 901 for a predetermined time, wherein the predetermined time is sufficient to allow the diffused region of the at least two miscible fluids to pass the collection region 903, to collect a portion of one of the miscible fluids, which is substantially free from contamination by any miscible fluids adjacent to the collected miscible fluid, into the second channel 902, and to stop the collection of one of the miscible fluids before a subsequent diffused region reaches the collection region. In some embodiments, the fluid flow control system is configured to determine the predetermined time by using a predetermined flow rate and/or a fixed volume displacement, as discussed herein. The fluid flow control system is also configured to repeat the flowing, collecting and stopping for each sample of miscible fluid which is substantially free from contamination by the other miscible fluids to be collected.

Although the diffusion minimization system shown in FIGS. 9A-9B is shown with a T-junction, the diffusion minimization system may comprise the one of the systems 101, 201, 301 and 401 of FIGS. 1-4, respectively, or may comprise alternate configurations having the same or similar characteristics and results of systems 101, 201, 301 and 401. A monitoring device 520 may be used to directly monitor the movement of the diffusion regions through the system, or the fluid velocity and/or volumetric displacement may be used to control flow of the fluids through channels for a time sufficient to ensure that the diffused regions would be past the collection point, as discussed herein.

While the invention has been particularly taught and described with reference to certain embodiments, those versed in the art will appreciate that modifications in form and detail may be made without departing from the spirit and scope of the invention. For example, the flow in the first microfluidic pathway A may be continuous or may be stopped while a given miscible fluid mixture flows into the second microfluidic pathway. Also, the flow into the second microfluidic pathway may be stopped or may flow in reverse while the diffused region between the original two microfluidic segments in the first channel is allowed to pass by the entrance to the second channel. In addition, each miscible fluid mixture, as referenced above, may comprise only one fluid, a homogenous mixture of multiple fluids or a heterogeneous mixture of multiple fluids. Further, the processes herein described may be repeated consecutively for multiple varied miscible fluid mixtures in the practice of the present invention.

Moreover, although embodiments of the system and method for minimizing or eliminating diffusion effects have been described in relation to a microfluidic system and method for nucleic acid analysis, the system and method of the present invention may be used to minimize or eliminate diffusion effects in any type of microfluidic system. And, although embodiments of the system and method for minimizing or eliminating diffusion effects have been described with the multiple, miscible fluid species collected in the second channel as being axially adjacent to each other, the fluid control system may provide gaps between the multiple fluid species collected in the second channel after the diffusion regions have been flushed.

The invention claimed is:

1. A method of collecting, from a continuous flow of two or more miscible fluids sequentially present in a channel, one or more samples that are substantially free from contamination by the other miscible fluids present in the channel, said method comprising:
   a. identifying and monitoring the position of a diffusion region between uncontaminated portions of a first miscible fluid and a second miscible fluid in a first channel;
   b. diverting the diffusion region into a second channel; and
   c. collecting a portion of the second miscible fluid which is substantially free from contamination by any miscible fluids adjacent to the second miscible fluid.

2. The method of claim 1, wherein the monitoring the position of the diffusion region includes monitoring a leading edge and a trailing edge of the diffusion region.

3. The method of claim 1, wherein the portion of the second miscible fluid is collected in a third channel.

4. The method of claim 3, wherein the position of the diffusion region is monitored in relation to an opening of the third channel.

5. The method of claim 3, wherein the diverting begins at or before a leading edge of the diffusion region reaches an opening of the third channel and ends after a trailing edge of the diffusion region passes the opening of the third channel.

6. The method of claim 3, wherein the second channel leads to a waste area.

7. The method of claim 1, wherein the diverting pulls fluid of the diffusion region from the edge of the first channel and the collecting pulls fluid of the portion of the second miscible fluid from the center of the first channel.

8. The method of claim 1, further comprising:
   d. identifying and monitoring the position of a diffusion region between uncontaminated portions of the second miscible fluid and a third miscible fluid in a first channel;
   e. diverting the diffusion region into the second channel; and
   f. collecting a portion of the third miscible fluid which is substantially free from contamination by any miscible fluids adjacent to the third miscible fluid.

9. The method of claim 1, further comprising:
   d. monitoring the amplification of DNA in the collected portion of the second miscible fluid; and
   e. monitoring the dissociation behavior of the amplified DNA in the collected portion of the second miscible fluid.

10. A genomic analysis system comprising:
    a microfluidic chip having:
        one or more microfluidic channels each passing through a diffusion minimization zone, a polymerase chain reaction processing zone, and a high-resolution thermal melt analysis zone; and
        a diffusion minimization system in fluid communication with one or more microfluidic channels, wherein the diffusion minimization system comprises:
            a first pathway through which a segmented flow of multiple, miscible fluid species enters;
            a second pathway through which one or more miscible fluid samples that are substantially free from contamination by adjacent miscible fluids present in the first pathway are collected and passed to the PCR processing zone and the HRTm analysis zone; and
            a third pathway through which one or more diffusion regions between adjacent fluid species of the segmented flow are diverted to a waste zone;
    a monitoring device that identifies and tracks the one or more diffusion regions present in the diffusion minimization zone of the microfluidic chip; and
    a fluid flow control system configured to control the flow of fluid through the diffusion minimization system and through the one or more microfluidic channels.

11. A method of collecting a sample from a continuous flow of two or more miscible fluids sequentially present in a channel, comprising:
    identifying the leading region of diffusion between two sequential fluids,
    monitoring the passage of the region of diffusion through the channel such that once the leading region of diffusion has passed an opening for a second channel a portion of the fluid is collected into a second channel,
wherein the collecting of fluid is stopped before the next sequential region of diffusion reaches the opening of the second channel.

12. The method of claim 11 wherein the collected sample is free from contamination by the other miscible fluid(s) present in the channel.

13. A method of collecting, from a continuous flow of two or more miscible fluids sequentially present in a first channel, one or more samples that are substantially free from contamination by the other miscible fluids present in the first channel, said method comprising:
  a. flowing the continuous flow of two or more miscible fluids through the first channel for a predetermined time, wherein the predetermined time is sufficient to allow the diffused region of the at least two miscible fluids to pass a collection region of the first channel, wherein the collection region of the first channel is a junction with a second channel;
  b. collecting a portion of one of the miscible fluids, which is substantially free from contamination by any miscible fluids adjacent to the collected miscible fluid, into the second channel; and
  c. stopping the collection of one of the miscible fluids before a subsequent diffused region reaches the collection region of the first channel.

14. The method of claim 13, wherein the predetermined time is determined by using a predetermined flow rate and/or a fixed volume displacement.

15. The method of claim 13, wherein steps a-c are repeated for each sample of miscible fluid which is substantially free from contamination by the other miscible fluids to be collected.

16. The method of claim 13, wherein the either one or both of the first and second channels is a microfluidic channel.

* * * * *